US012686867B2

(12) United States Patent
Hong et al.

(10) Patent No.: US 12,686,867 B2
(45) Date of Patent: Jul. 21, 2026

(54) RNAi AGENT TARGETING MYD88 AND USE THEREOF

(71) Applicant: OliX Pharmaceuticals, Inc., Suwon-si (KR)

(72) Inventors: Sun Woo Hong, Gyeonggi-do (KR); June Hyun Park, Gyeonggi-do (KR)

(73) Assignee: OliX Pharmaceuticals, Inc., Suwon-si (KR)

( * ) Notice: Subject to any disclaimer, the term of this patent is extended or adjusted under 35 U.S.C. 154(b) by 842 days.

(21) Appl. No.: 17/927,427

(22) PCT Filed: Aug. 13, 2020

(86) PCT No.: PCT/KR2020/010787
§ 371 (c)(1),
(2) Date: Nov. 23, 2022

(87) PCT Pub. No.: WO2021/241803
PCT Pub. Date: Dec. 2, 2021

(65) Prior Publication Data

US 2024/0093188 A1 Mar. 21, 2024

(30) Foreign Application Priority Data

May 26, 2020 (KR) ........................ 10-2020-0063281

(51) Int. Cl.
*C12N 15/113* (2010.01)
*A61P 27/02* (2006.01)

(52) U.S. Cl.
CPC ............ *C12N 15/113* (2013.01); *A61P 27/02* (2018.01); *C12N 2310/11* (2013.01); *C12N 2310/315* (2013.01); *C12N 2310/3515* (2013.01)

(58) Field of Classification Search
None
See application file for complete search history.

(56) References Cited

U.S. PATENT DOCUMENTS

| | | | |
|---|---|---|---|
| 8,022,199 | B2 | 9/2011 | Khvorova et al. |
| 9,637,742 | B2 | 5/2017 | Lee |
| 10,059,949 | B2 | 8/2018 | Lee et al. |
| 10,064,801 | B2 | 9/2018 | Hong et al. |
| 10,125,362 | B2 | 11/2018 | Hong |
| 10,214,744 | B2 | 2/2019 | Lee |
| 10,301,628 | B2 | 5/2019 | Lee et al. |
| 10,358,648 | B2 | 7/2019 | Lee et al. |
| 10,512,600 | B2 | 12/2019 | Hong et al. |
| 10,519,449 | B2 | 12/2019 | Lee et al. |
| 10,590,423 | B2 | 3/2020 | Lee et al. |
| 10,829,760 | B2 | 11/2020 | Lee |
| 10,829,761 | B2 | 11/2020 | Lee et al. |
| 10,883,105 | B2 | 1/2021 | Hong |
| 10,947,541 | B2 | 3/2021 | Lee et al. |
| 11,040,057 | B2 | 6/2021 | Lee et al. |
| 2008/0113376 | A1 | 5/2008 | Khvorova et al. |
| 2010/0092486 | A1 | 4/2010 | Kandimalla et al. |
| 2012/0016007 | A1 | 1/2012 | Lee et al. |
| 2012/0238017 | A1 | 9/2012 | Lee et al. |
| 2013/0035368 | A1* | 2/2013 | Avkin-Nachum ...... A61P 11/00 536/24.5 |
| 2013/0273657 | A1 | 10/2013 | Lee |
| 2013/0324591 | A1 | 12/2013 | Avkin-Nachum et al. |
| 2015/0111948 | A1 | 4/2015 | Hong |
| 2016/0333356 | A1 | 11/2016 | Feinstein et al. |
| 2016/0355805 | A1 | 12/2016 | Avkin-Nachum et al. |
| 2017/0027837 | A1 | 2/2017 | Hong et al. |
| 2017/0137828 | A1 | 5/2017 | Lee et al. |
| 2017/0218374 | A1 | 8/2017 | Lee et al. |
| 2017/0218376 | A1 | 8/2017 | Lee et al. |
| 2017/0298358 | A1 | 10/2017 | Lee et al. |
| 2017/0335326 | A1 | 11/2017 | Lee |
| 2018/0127747 | A1 | 5/2018 | Lee et al. |
| 2018/0327755 | A1 | 11/2018 | Lee et al. |
| 2019/0002881 | A1 | 1/2019 | Hong |
| 2019/0038538 | A1 | 2/2019 | Hong et al. |
| 2019/0119672 | A1 | 4/2019 | Lee et al. |
| 2019/0177732 | A1 | 6/2019 | Lee |
| 2019/0321388 | A1 | 10/2019 | Lee et al. |
| 2019/0367925 | A1 | 12/2019 | Lee et al. |
| 2020/0109405 | A1 | 4/2020 | Lee et al. |

(Continued)

FOREIGN PATENT DOCUMENTS

| | | | |
|---|---|---|---|
| CN | 104450710 | B | 6/2018 |
| CN | 108699556 | A | 10/2018 |

(Continued)

OTHER PUBLICATIONS

Baran-Rachwalska et al. Journal of Controlled Release 326, 192-202 (Year: 2020).*

(Continued)

*Primary Examiner* — Brian Whiteman

(74) *Attorney, Agent, or Firm* — Morgan, Lewis & Bockius LLP

(57) ABSTRACT

The present disclosure relates to an RNAi-inducing nucleic acid molecule and use thereof. An aspect of the disclosure relates to an RNAi-inducing nucleic acid molecule for inhibiting expression of myeloid differentiation primary response gene 88 (MyD88). Another aspect of the present disclosure relates to a pharmaceutical composition for treating or preventing age-related macular degeneration, comprising the RNAi-inducing nucleic acid molecule.

8 Claims, 8 Drawing Sheets

Specification includes a Sequence Listing.

(56) References Cited

U.S. PATENT DOCUMENTS

| | | | |
|---|---|---|---|
| 2020/0123548 | A1 | 4/2020 | Lee et al. |
| 2021/0207137 | A1 | 7/2021 | Hong |
| 2021/0285001 | A1 | 9/2021 | Lee |
| 2022/0380774 | A1 | 12/2022 | Lee et al. |

FOREIGN PATENT DOCUMENTS

| | | | |
|---|---|---|---|
| KR | 10-2011-0036966 | A | 4/2011 |
| KR | 10-2018-0071362 | A | 6/2018 |
| WO | WO 2009/039173 | A1 | 3/2009 |

OTHER PUBLICATIONS

International Search Report & Written Opinion, PCT Application No. PCT/KR2020/010787, dated Dec. 12, 2021, 11 pages.

Kerur, et al., Investigative Ophthalmology & Visual Science, vol. 55, Issue 13, "Myd88 as a therapeutic target for choroidal neovascularization" (Apr. 30, 2024).

* cited by examiner

Western blot analysis for MyD88
in normal mouse RPE on D7 post IVT

| IVT (8 μg/eye) → WB (D7) | | | | | | | | | | | |
|---|---|---|---|---|---|---|---|---|---|---|---|
| SCR* | | | OLX301A-110-21 | | | OLX301A-110-22 | | | OLX301A-110-23 | | |
| 1 | 2 | 3 | 1 | 2 | 3 | 1 | 2 | 3 | 1 | 2 | 3 |

Western blot analysis for MyD88
in laser-injured mouse RPE on D7 post IVT

*,** P < 0.05, 0.001, vs PBS
§ P < 0.05, vs OLX10020 at each dose
Student t test (two-tailed)
Mean ± S.D.

RNAi AGENT TARGETING MYD88 AND USE THEREOF

CROSS-REFERENCE TO RELATED APPLICATIONS

This application is a 35 U.S.C. § 371 national stage application of PCT/KR2020/010787, filed on Aug. 13, 2020, and claims priority to, and the benefit of, Korean Patent Application No. 10-2020-0063281, filed on May 26, 2020, the contents of which are incorporated herein by reference in their entireties.

SEQUENCE LISTING SUBMISSION VIA EFS-WEB

A computer readable text file, entitled "OLX-015_116825-5015", created on or about Jan. 5, 2023 with a file size of about 8,192 bytes contains the sequence listing for this application and is hereby incorporated by reference in its entirety.

TECHNICAL FIELD

The present disclosure relates to a nucleic acid molecule for treating or preventing disease via the phenomenon of RNA interference and use thereof.

BACKGROUND ART

Age-related macular degeneration (AMD) is a disease which is caused by the degeneration of the inner layers of retinal pigment epithelia in the macula of eyes and results in vision loss. The macula is a small area in the retina consisting of photo-sensitive tissue covering the inside of eyes and plays an important role in central vision. AMD is one of the most leading causes of vision loss worldwide. AMD occurs as "wet" and "dry" forms. The wet AMD is caused by abnormal growth of blood vessels in the retina. In wet AMD, an increase in the amount of vascular endothelial growth factor (VEGF) contributes to neovascularization, and treatment options include use of a VEGF inhibitor. However, within several years of the treatment, many patients treated with a VEGF inhibitor develop geographic atrophy (GA) which is a major symptom of later dry macular degeneration. The pathogenesis of dry AMD is not clearly discovered and there is no medical treatment available for dry AMD to date. Thus, there is a need to develop a therapeutic agent capable of treating both dry macular degeneration and wet macular degeneration. Accordingly, although development of a therapeutic agent effective for both dry AMD and wet AMD is required, it has been incomplete.

Therefore, the present inventors have made extensive research efforts to develop a novel safe drug to treat patients with dry AMD and further wet AMD and have found an RNA agent using RNA interference technology.

DESCRIPTION OF EMBODIMENTS

Technical Problem

An object of the present disclosure is to provide a RNAi agent targeting MyD88.

Another object of the present disclosure is to provide a RNAi agent for treating dry and/or wet AMD and medical use thereof.

Other objects and advantages of the present disclosure will become more obvious herein in the specification together with appended claims and drawings. Descriptions of details apparent to those skilled in the art having ordinary knowledge in this technical field or relevant field will be omitted herein.

Solution to Problem

An aspect of the present disclosure to achieve the above-described objects is to provide a double stranded RNAi-inducing nucleic acid molecule targeting MyD88.

Another aspect of the present disclosure is to provide a pharmaceutical composition for treating or preventing dry and/or wet AMD including the RNAi-inducing nucleic acid molecule as an active ingredient.

Advantageous Effects of Disclosure

The siRNA of according to an aspect may bind to and degrade mRNA encoding MyD88, which is a protein related to an eye disease, i.e., AMD, thereby inhibiting expression of the protein while decreasing side effects such as non-specific immune responses and off-target effect. Thus, the nucleic acid molecule according to an aspect may be used as an active ingredient of a pharmaceutical composition for treating and preventing dry and/or wet AMD.

MODE OF DISCLOSURE

Figure 1A:
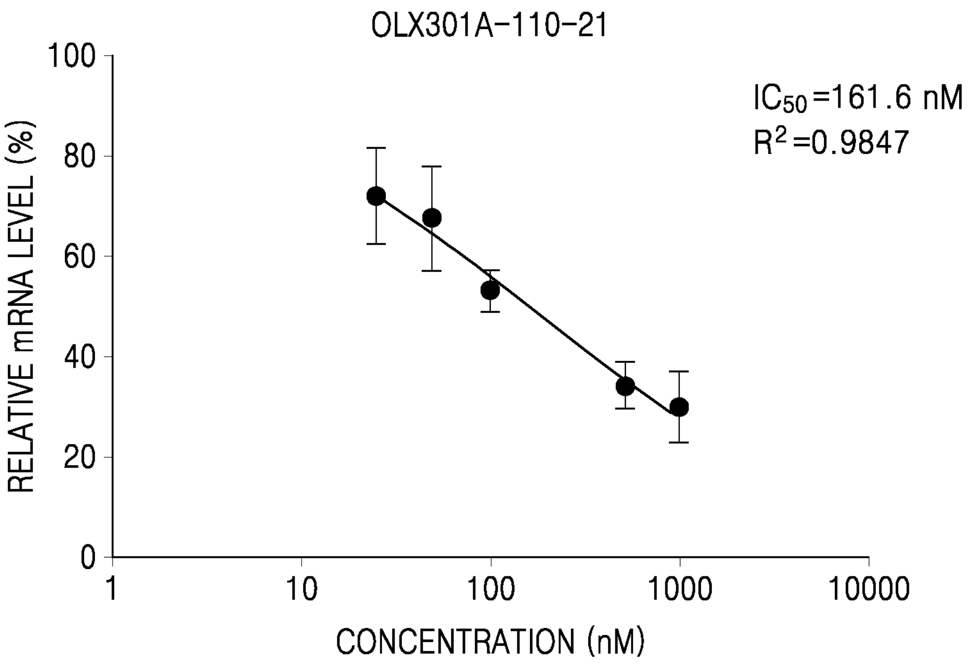
FIGS. 1A to 1C show changes in MyD88 mRNA levels of the cells by treating OLX301A-110-21, OLX301A-110-22, and OLX301A-110-23 of cell, which are siRNAs according to the present disclosure.

Each description and embodiment disclosed in the present disclosure may be applied herein to describe different descriptions and embodiments. In other words, all combinations of various components disclosed in the present disclosure are included within the scope of the present disclosure. Furthermore, the scope of the present disclosure should not be limited by the detailed descriptions provided below.

According to an aspect of the disclosure, provided is a RNAi-inducing nucleic acid molecule including a sense strand and an antisense strand, wherein:

- the sense strand has 15 to 17 nucleotides in length; at least 15 contiguous nucleotides of the sense strand are complementary to the antisense strand;
- the sense strand comprises at least one chemical modification; and the antisense strand includes the sequence selected from the group of (A) to (D) (5'->3'):

```
(A)
                                        (SEQ ID NO: 5)
P-mUGGUCUGGAAGmUmCAmC*A*mU*mU*mC,

(B)
                                        (SEQ ID NO: 6)
P-mUfGmGfUmCfUmGfGmAfAmGfUmCfAmC*fA*mU*fU*mC,

(C)
                                        (SEQ ID NO: 7)
P-mUGmGUCUmGmGmAmAmGUCAC*mA*U*U*C,
and

(D)
                                        (SEQ ID NO: 8)
P-mUGGfUfCfUGGAAGfUfCAfC*A*fU*fU*fC,
```

wherein * is a phosphorothioate linkage, m is 2'-O-methyl, f is 2'-fluoro, and P is 5'-phosphate linkage.

According to another aspect of the present disclosure, provided is a RNAi-inducing nucleic acid molecule including a sense strand and an antisense strand, wherein:

the antisense strand has 19 to 21 nucleotides in length; at least 15 contiguous nucleotides of the antisense strand are complementary to the sense strand; the antisense strand comprises at least one chemical modification; and the sense strand comprises the sequence selected from the group of (a) to (c) (5'->3'):

```
(a)
                                        (SEQ ID NO: 15)
mUmGUGACUUCCAGAC*mC*mA*Lp,

(b)
                                        (SEQ ID NO: 9)
mUGmUGmACmUUmCCmAGmAC*mC*A*Lp,
and

(c)
                                        (SEQ ID NO: 10)
mUGmUGAmCmUmUmCmCAGAmC*mC*A*Lp,
```

wherein * is a phosphorothioate linkage, m is 2'-O-methyl, and Lp is a lipophilic moiety.

According to another aspect of the present disclosure, provided is a RNAi-inducing nucleic acid molecule, including double-stranded siRNA which inhibits expression of MyD88, wherein the siRNA includes an antisense strand of SEQ ID No: 1 (5'-UGGUCUGGAAGUCACAUUC-3') and a sense strand of SEQ ID No: 2 (5'-UGUGACUUCCA-GACCA-3'), the antisense strand and the sense strand are complementary to each other to form a blunt end at 5'-end of the antisense strand and 3'-end of the sense strand; and a lipophilic moiety selected from the group consisting of cholesterol, tocopherol, stearic acid, retinoic acid, Docosahexaenoic acid (DHA), palmitic acid, linoleic acid, linolenic acid, and a long chain fatty acid of at least 10 carbon atoms is introduced at 3'-end of the sense strand.

RNAi-Inducing Nucleic Acid Molecule

As used herein, the term "RNA interference" or "RNAi" refers to a biological process generally known in the fields of technologies to inhibit or decrease gene expression in cells by causing destruction of a certain target RNA and being mediated by a sequence-specific nucleic acid molecule. Also, the term RNAi may be equivalent to any other term used to describe sequence-specific RNA interference techniques such as gene silencing after transcription, translation inhibition, transcription inhibition, or epigenetics. For example, the siRNA molecule may be used in post-transcriptional or pre-transcriptional gene silencing. In a non-limiting example, regulation of gene expression by a siRNA molecule may result from siRNA-mediated cleavage of mRNA by RNA-induced silencing complex (RISC).

As used herein, the term "RNAi-inducing nucleic acid molecule", "short interfering RNA", "siRNA molecule", or "siRNA" refers to any nucleic acid molecule capable of inhibiting or decreasing gene expression or viral replication by mediating the RNA interference in a sequence-specific manner. The term may refer to an individual nucleic acid molecule, a plurality of nucleic acid molecules, or a pool of the nucleic acid molecules. The siRNA may be an asymmetric double-stranded nucleic acid molecule including a self-complementary sense and an antisense strand.

As used herein, the term "gene" should be considered in the broadest sense and may encode a structural protein or a regulatory protein. In this regard, the regulatory protein includes a protein involved in a transcription factor, a heat shock protein, or DNA/RNA replication, transcription and/or translation. In the present disclosure, a target gene to be subjected to expression inhibition is included in a viral genome and may be integrated into an animal gene or exist as an extrachromosomal component.

As used herein, the term "antisense strand" indicates a meaning commonly acceptable in the art. With regard to the siRNA molecule described herein, the term may also refer to a nucleotide sequence of an siRNA molecule having complementarity to MyD88 RNA. Also, the antisense strand of the siRNA molecule may include a nucleic acid sequence having complementarity to a sense strand of the siRNA molecule. The antisense strand of the siRNA molecule may also be referred to as an antisense region or a guide strand.

As used herein, the term "sense strand" indicates a meaning commonly acceptable in the art. With regard to the siRNA molecule, the term may refer to a nucleotide sequence of the siRNA molecule having complementarity to the antisense strand of the siRNA molecule. Also, the sense strand of the siRNA molecule may include a nucleic acid sequence having homology or sequence identity with a target nucleic acid sequence. In addition, in an embodiment, the sense strand of the siRNA molecule may be referred to as a sense region or a passenger strand.

As used herein, the term "complementarity" or "complementary" refers to a meaning commonly acceptable in the art. The term may refer to formation or presence of hydrogen bonds between one nucleic acid sequence and the other nucleic acid sequence via traditional Watson-Crick base pairing or other non-traditional types of pairing described herein. Complete complementarity may indicate that all contiguous residues of a first nucleic acid sequence form hydrogen bonds with the same number of contiguous residues of a second nucleic acid sequence. Partial complementarity may include various mismatches or non-base paired nucleotides (e.g., 1, 2, 3, 4, 5, 6, 7, 8, 9, 10, or more mismatches, non-nucleotide linkers, or non-base paired nucleotides) in a nucleic acid molecule. The partial complementarity may result in bulges, loops, overhang, or blunt end between a sense strand or sense region and an antisense strand or antisense region of a nucleic acid molecule, or between an antisense strand or antisense region of a nucleic acid molecule and a target nucleic acid molecule corresponding thereto.

As used herein, the term "blunt end" refers to a meaning commonly acceptable in the art. With respect to the nucleic acid molecule of the present disclosure, the term may refer to an end of a double-stranded siRNA molecule without overhanging nucleotides. In the siRNA molecule disclosed herein, the 5'-end of the antisense strand and the 3'-end of the sense strand may form a blunt end.

RNAi-Inducing Nucleic Acid Molecule to Inhibit Expression of MyD88

"MyD88" is myeloid differentiation primary response gene 88 and is also referred to as innate immune signal transduction adaptor. The MyD88 has been known to contribute to signal transduction in immune cells and be closely related to eye diseases such as macular degeneration. The MyD88 protein may be interpreted as including naturally occurring wild-type MyD88 and functional variants thereof, and sequences of the MyD88 protein or a gene encoding the same may be obtained from known database such as GenBank database of the National Center for Biotechnology Information (NCBI).

As used herein, the term "expression" refers to a meaning commonly acceptable in the art. In general, the term may refer to a process of producing a protein from a gene. The expression includes, but is not limited to, transcription, splicing, post-transcriptional modification, or translation. As used herein, an expression level may be determined or monitored by detection in the mRNA or protein level.

The term "inhibition" or "decrease" used in relation to expression of MyD88 gene in a subject refers to a statistically significant decrease compared to non-treated or normal controls. The decrease may be, for example, a decrease by at least 30%, 35%, 40%, 45%, 50%, 55%, 60%, 65%, 70%, 75%, 80%, 85%, 90%, or more than 95%, but may be less than a detection level according to detection or measurement methods.

The siRNA refers to small interfering RNA and is involved in function of RNA interference (RNAi). RNAi is an intracellular gene-regulating mechanism first discovered in Caenorhabditis elegans in 1998 and the mechanism of action thereof is known to induce target gene degradation as an antisense strand of a double-stranded RNA introduced into a cell complementarily binds to mRNA of the target gene. RNAi is the most popular candidate for drug development technologies in recent years.

However, contrary to this possibility, side effects and disadvantages of siRNA have been continuously reported. For development of RNAi-based therapeutic agent, problems such as 1) absence of effective delivery system 2) off-target effect 3) immune response induction, and 4) saturation of cellular RNAi machinery need to be overcome. Although siRNA is an effective method for directly regulating expression of a target gene, it is difficult to develop therapeutic agents due to these problems. In this regard, asymmetric shorter duplex siRNA (asiRNA) has an asymmetric RNAi-inducing structure with a shorter double helix than a 19+2 structure of conventional siRNA. It is a technology that overcomes problems identified in the conventional siRNA structure technology such as off-target effect, saturation of RNAi mechanism, and immune response by TLR3, and thus it is possible to develop new RNAi drugs with low side effects.

Based thereon, the present embodiment provides asymmetric siRNA (asiRNA) including a sense strand and an antisense strand complementary to the sense strand. Because siRNA according to an embodiment does not cause problems such as off-target effect and saturation of RNAi mechanism, expression of MyD88 gene may be effectively inhibited to a desired level while stably maintaining high delivery efficiency.

In an embodiment, an asiRNA targeting MyD88 is designed and prepared. After transfecting MyD88-expressing cell with the asiRNA, RNAi-inducing nucleic acid molecules having excellent knockdown efficiency, i.e., MyD88 asiRNA, were selected.

In an embodiment, the RNAi-inducing nucleic acid molecule includes an antisense strand of SEQ ID No: 1 and a sense strand of SEQ ID No: 2, each strand may be introduced with chemical modification.

Also, the 5'-end of the antisense strand and the 3'-end of the sense strand may form a blunt end.

RNAi-Inducing Nucleic Acid Molecule Introduced with Chemical Modification

In the RNAi-inducing nucleic acid molecule, the sense strand or the antisense strand may include at least one chemical modification.

Since general siRNA cannot pass through cell membrane due to high negative charge and high molecular weight caused by a phosphate backbone structure and is degraded and removed from the blood, it is difficult to deliver a sufficient amount thereof for inducing RNAi at an actual target site. While various in vitro delivery methods with high efficiency using cationic lipids and cationic polymers have been developed to date, in the case of in vivo, it is difficult to deliver siRNA with an efficiency as high as that of in vitro delivery and there is a problem that siRNA delivery efficiency decreases due to interactions with various proteins present in the living body.

Thus, the present embodiment provides a RNAi-inducing nucleic acid molecule having cell-penetrating ability by introducing a chemical modification into the asiRNA structure, more particularly, a cell penetrating asymmetric siRNA (cp-asiRNA) capable of effectively performing intracellular delivery without a separate transmitter.

Meanwhile, the above-described chemical modification may impart the following functionality:

(i) Introduction of the lipophilic moiety into the 3'-end of the sense strand may facilitate penetration of siRNA through the cell membrane, (ii) Substitution of the phosphate backbone adjacent to the end of the sense strand or the antisense strand with phosphorothioate, or the like may impart resistance to hydrolase outside nucleic acids and enables the uptake into cells and biological use of siRNA in vivo. (iii) Substitution of the —OH group at a 2' carbon position of a sugar structure with a methyl, methoxy, or the like may impart resistance to nuclease, decrease siRNA immunogenicity, and reduce the off-target effect, and (iv) Substitution at a 2' carbon position of the sugar structure with a fluoro may impart stability to a double strand, improve stability in serum, and enable effective silencing in vitro and in vivo.

In an embodiment, the antisense strand includes the sequence selected from the group (A) to (D) (5'->3'), wherein * is a phosphorothioate linkage, m is 2'-O-methyl, f is 2'-fluoro, and P is 5'-phosphate linkage:

```
(A)
                                        (SEQ ID NO: 5)
P-mUGGUCUGGAAGmUmCAmC*A*mU*mU*mC,

(B)
                                        (SEQ ID NO: 6)
P-mUfGmGfUmCfUmGfGmAfAmGfUmCfAmC*fA*mU*fU*mC,
```

-continued

```
(C)
                                            (SEQ ID NO: 7)
P-mUGmGUCUmGmGmAmAmGUCAC*mA*U*U*C,
or

(D)
                                            (SEQ ID NO: 8)
P-mUGGfUfCfUGGAAGfUfCAfC*A*fU*fU*fC.
```

In an embodiment, the sense strand has 15 to 17 nucleotides in length, at least 15 contiguous nucleotides of the sense strand are complementary to the antisense strand; and the sense strand may include at least one chemical modification. The sense strand includes the sequence selected from the group of (a) to (c) (5'->3'), wherein * is a phosphorothioate linkage, m is 2'-O-methyl, and Lp is a lipophilic moiety:

```
(a)
                                            (SEQ ID NO: 15)
mUmGUGACUUCCAGAC*mC*mA*Lp,

(b)
                                            (SEQ ID NO: 9)
mUGmUGmACmUUmCCmAGmAC*mC*A*Lp,
or

(c)
                                            (SEQ ID NO: 10)
mUGmUGAmCmUmUmCmCAGAmC*mC*A*Lp.
```

The lipophilic moiety may be selected from the group consisting of cholesterol, tocopherol, stearic acid, retinoic acid, docosahexaenoic acid (DHA), palmitic acid, linoleic acid, linolenic acid, and a long chain fatty acid of at least 10 carbon atoms, preferably cholesterol, DHA, or palmitic acid. More preferably, palmitic acid may be used.

In an embodiment, the sense strand includes one selected from the following sense strands, wherein * is a phosphorothioate linkage, m is 2'-O-methyl, chol is 3'-cholesterol linkage, and PA is 3'-palmitic acid linkage:

```
(d)
                                            (SEQ ID NO: 11)
mUmGUGACUUCCAGAC*mC*mA*chol,

(e)
                                            (SEQ ID NO: 12)
mUGmUGmACmUUmCCmAGmAC*mC*A*chol,

(f)
                                            (SEQ ID NO: 13)
mUGmUGAmCmUmUmCmCAGAmC*mC*A*chol,

(g)
                                            (SEQ ID NO: 14)
mUmGUGACUUCCAGAC*mC*mA*PA,

(h)
                                            (SEQ ID NO: 16)
mUGmUGmACmUUmCCmAGmAC*mC*A*PA,
or

(i)
                                            (SEQ ID NO: 17)
mUGmUGAmCmUmUmCmCAGAmC*mC*A*PA.
```

According to another aspect of the present disclosure, provided is a pharmaceutical composition for treating or preventing eye diseases including the RNAi-inducing nucleic acid molecule as an active ingredient.

Since the pharmaceutical composition includes or uses the above-described RNAi-inducing nucleic acid molecule, descriptions in common therebetween will be omitted to avoid undue complexity in the present specification.

Eye Disease

The pharmaceutical composition has a function of inhibiting abnormal angiogenesis by inhibiting expression of MyD88 gene and thus may be used as an active ingredient of a pharmaceutical composition for treating or preventing eye diseases accompanied by blood vessel abnormalities.

The eye disease may be, for example, macular degeneration. In this regard, the "macular degeneration" is an eye disease in which new blood vessels abnormally grow causing damages to maculae accompanied by symptoms affecting vision. Macular degeneration occurs mainly in the age group of 50 years or older and is divided into nonexudative macular degeneration (dry form) and exudative macular degeneration (wet form). Particularly, in the case of wet macular degeneration, vision loss may be caused. Although the cause is not accurately discovered, age is known as a risk factor and environmental factors include smoking, hypertension, obesity, genetic predisposition, overexposure to UV light, low blood levels of antioxidants, and the like.

Pharmaceutical Composition

As used herein, the term "active ingredient" refers to an ingredient affecting beneficial or desired clinical or biochemical results and used in an appropriate effective amount. Specifically, the effective ingredient may refer to an agent, an active agent, or a nucleic acid molecule used in an effective amount.

The effective amount may be administered once or more times and refer to an appropriate amount for preventing disease or alleviating symptoms, decreasing the range of the disease, stabilizing the disease state (i.e., not worsening), delaying or reducing progression of the disease, or improving the disease state or temporarily alleviating and reducing (partially or entirely) the disease state, without being limited thereto.

As used herein, the term "prevention" refers to any action that blocks occurrence of a disease, inhibits the disease, or delaying the progression of the disease. For example, the prevention refers to inhibiting occurrence of the eye disease or characteristic conditions thereof, interfering the occurrence, or defending or protecting against the eye disease or characteristic conditions thereof.

As used herein, the term "treatment" refers to both therapeutic treatment and preventive and precaution approaches. The term also refers to any action in which symptoms of disease are alleviated or beneficially changed. For example, the treatment is preventing, decreasing, or alleviating the eye disease or characteristic conditions thereof or delaying (weakening) progression of the eye disease or characteristic conditions thereof.

As used herein, the term "effective amount" indicates to a meaning commonly acceptable in the art. The term may refer to an amount of a molecule, compound, or ingredient deriving desired biological response (e.g., beneficial response) in cells, tissue, systems, animals, or humans sought by researchers, veterinarians, physicians, or other clinicians. Specifically, the term "therapeutically effective amount" refers to an amount of a molecule, compound, or ingredient deriving desired medical response to the extent that a particular clinical treatment may be considered effective with therapeutic changes in measurable parameters related to disease or disorder. The therapeutically effective amount of a drug for treatment of disease or disorder may be an amount required to cause therapeutically related changes in the parameter.

The pharmaceutical composition including the nucleic acid molecule according to the present disclosure may be administered intraocularly. Intraocular administration of the nucleic acid molecule may be conducted by injection into an eye or direct (e.g., topical) administration as long as the route of administration allows the nucleic acid molecule to enter the eye. In addition to the topical administration into the eye, appropriate routes of intraocular administration include intravitreal, intraretinal, subretinal, subtenon, peri-orbital, and retro-orbital, intraconjunctival, subconjunctival, trans-corneal, and trans-scleral administration.

The "pharmaceutically acceptable composition" or "pharmaceutically acceptable formulation" may refer to a composition or formulation capable of effectively distributing the nucleic acid molecule to the most appropriate physical position where a desired activity is to be obtained.

According to another aspect of the present disclosure, provided is a method of treating an eye disease, the method including administering a therapeutically effective amount of the pharmaceutical composition to an individual.

Since the method of treating the eye disease includes the above-described RNAi-inducing nucleic acid molecule or pharmaceutical composition, descriptions in common therebetween will be omitted to avoid undue complexity in the present specification.

As used herein, the term "individual" refers to a subject in need of treatment fora disease, particularly, an eye disease and more particularly may include mammals such as humans or non-human primates, mice, dogs, cats, horses, cattle, sheep, pigs, goats, camels, and antelopes.

Hereinafter, the present disclosure will be described in more detail with reference to the following examples. However, these examples are merely presented to exemplify the present disclosure, and the scope of the present disclosure is not limited thereto.

Example 1. siRNA Sequence and Synthesis

In the present example, siRNAs targeting MyD88 were synthesized. The siRNAs were prepared by inducing various chemical modifications (2'OMe, PS, and Fluoro) and by introducing a lipophilic moiety such as cholesterol and palmitic acid into the 3'-end of the sense strand (Refer to Table 1), and preparation methods thereof are well known in the art. Specifically, in the present example, in order to introduce cholesterol and PA, as a lipophilic moiety, cholesterol-TEG-CPG (manufactured by LGC Prime Synthesis) and PA-linker-CPG (manufactured by LGC LINK, refer to Table 3 below).

TABLE 1

| Type of siRNA | Sequence (5'→3') Sense (16 mer) | Anti-sense (19 mer) |
|---|---|---|
| OLX301A-110-3 | mUmGUGACUUCCAGAC*mC*mA*chol (SEQ ID NO: 11) | P-mUGGUCUGGAAGmUmCAmC*A*mU*mU*mC (SEQ ID NO: 5) |
| OLX301A-110-5 | mUmGUGACUUCCAGAC*mC*mA*chol (SEQ ID NO: 11) | P-mUfGmGfUmCfUmGfGmAfAmGfUmCfAmC*fA*mU*fU*mC (SEQ ID NO: 6) |
| OLX301A-110-7 | mUGmUGmACmUUmCCmAGmAC*mC*A*chol (SEQ ID NO: 12) | P-mUGmGUCUmGmGmAmAmGUCAC*mA*U*U*C (SEQ ID NO: 7) |
| OLX301A-110-13 | mUGmUGAmCmUmUmCmCAGAmC*mC*A*chol (SEQ ID NO: 13) | P-mUGGUCUGGAAGmUmCAmC*A*mU*mU*mC (SEQ ID NO: 5) |
| OLX301A-110-14 | mUGmUGAmCmUmUmCmCAGAmC*mC*A*chol (SEQ ID NO: 13) | P-mUGGfUfCfUGGAAGfUfCAfC*A*fU*fU*fC (SEQ ID NO: 8) |
| OLX301A-110-21 | mUmGUGACUUCCAGAC*mC*mA*PA (SEQ ID NO: 14) | P-mUfGmGfUmCfUmGfGmAfAmGfUmCfAmC*fA*mU*fU*mC (SEQ ID NO: 6) |
| OLX301A-110-22 | mUGmUGmACmUUmCCmAGmAC*mC*A*PA (SEQ ID NO: 16) | P-mUGmGUCUmGmGmAmAmGUCAC*mA*U*U*C (SEQ ID NO: 7) |
| OLX301A-110-23 | mUGmUGAmCmUmUmCmCAGAmC*mC*A*PA (SEQ ID NO: 17) | P-mUGGUCUGGAAGmUmCAmC*A*mU*mU*mC (SEQ ID NO: 5) |

Meanwhile, chemical modifications indicated by "*", "m", "f", "chol", and "PA" in Table 1 are as shown in Table 2, and chemical modifications indicated by "chol" and "PA" indicate that cholesterol and palmitic acid (introduced in the form of palmitoyl) introduced into the 3'-end, respectively.

TABLE 2

| Notation | Chemical modification |
|---|---|
| * | phosphorothioated bond |
| m | 2'-O-methyl |
| f | 2'-fluoro |
| chol | cholesterol |
| PA | palmitic acid-introduced in the form of palmitoyl |

TABLE 3

| PA-linker-CPG | Manufacturer |
|---|---|
| 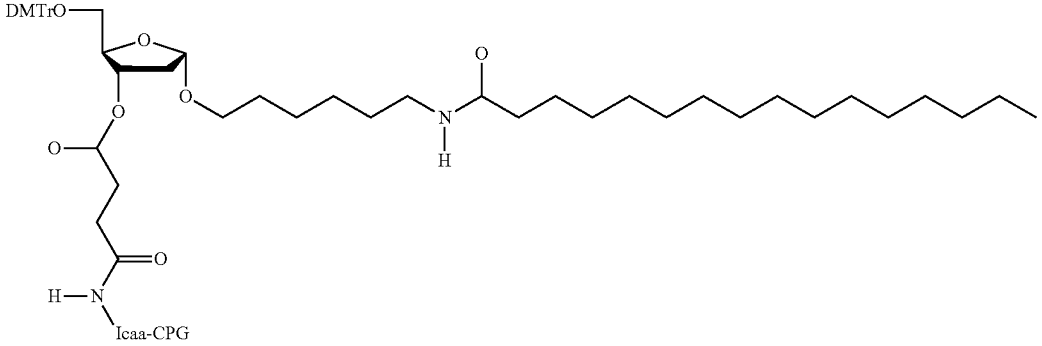 | LGC LINK (Scotland, UK) |

Example 2. Evaluation of MyD88 mRNA Level by cp-asiRNA Treatment—In Vitro Knockdown Analysis (1) Analysis According to Treatment with OLX301A-110-3, OLX301A-110-5, OLX301A-110-7, OLX301A-110-13, and OLX301A-110-14

In order to identify the effect on inhibiting expression of MyD88 mRNA, ARPE-19 cells were treated with 100 nM of each of the siRNAs, i.e., each of OLX301A-110-3, OLX301A-110-5, OLX301A-110-7, OLX301A-110-13, and OLX301A-110-14 and incubated (free uptake), and then expression levels of MyD88 mRNA were measured by real-time qPCR. Specifically, the ARPE-19 cells were seeded on 24-well plates at a density of $3\times10^4$ cells/well. After 24 hours, 100 nM of cp-siRNA was added thereto and the cells were incubated under Opti-MEM media conditions. After 24 hours, total RNA was extracted by using a Tri-RNA reagent (FAVORGEN), and cDNA was synthesized using a high-capacity cDNA reverse transcription kit (Applied Biosystems). Then, expression levels of MyD88 gene were identified by CFX Connect Real-Time PCR Detection System (BioRad) using TB Green Premix Ex Taq (Takara, RR420A) and primers shown in Table 4 (Refer to Table 5).

TABLE 4

| Name | | Sequence (5'→3') |
|---|---|---|
| Human | Forward | GCTCATCGAAAAGAGGTGCC (SEQ ID NO: 3) |
| MyD88 | Reverse | GGTTGGTGTAGTCGCAGACA (SEQ ID NO: 4) |

TABLE 5

| | Type of siRNA | | | | | |
|---|---|---|---|---|---|---|
| | NT | OLX301A-110-3 | OLX301A-110-5 | OLX301A-110-7 | OLX301A-110-13 | OLX301A-110-14 |
| Relative mRNA level(%) | 100 | 30.06 | 9.43 | 17.70 | 34.23 | 5.58 |

(2) Analysis According to Treatment with OLX301A-110-21, OLX301A-110-22, and OLX301A-110-23

Experiments were performed to identify as described below whether the siRNAs synthesized in Example 1, OLX301A-110-21, OLX301A-110-22, and OLX301A-110-23, inhibit expression of MyD88.

Figure 1B:
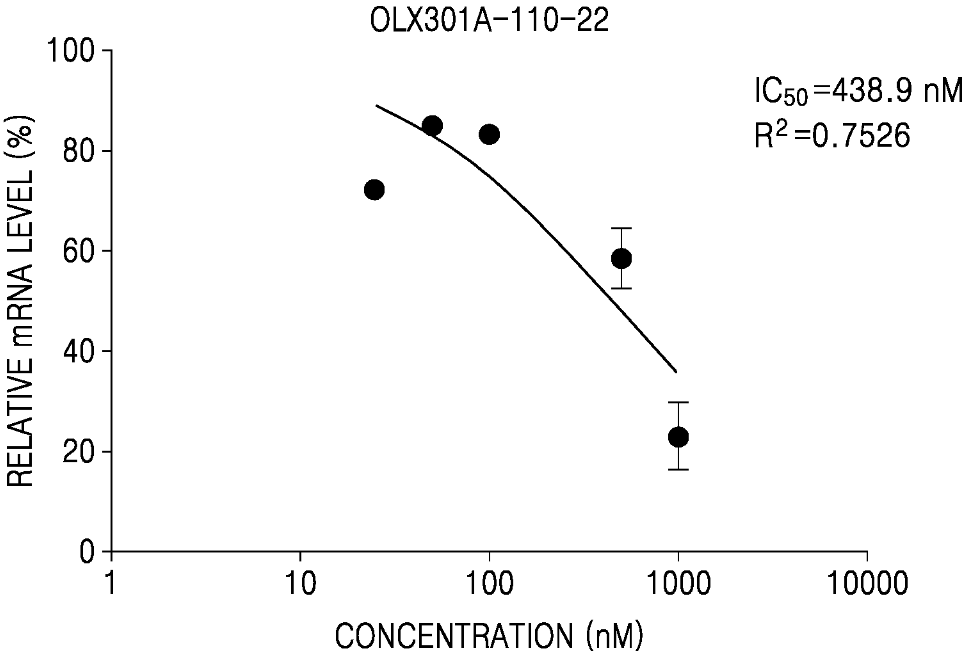
Figure 1C:
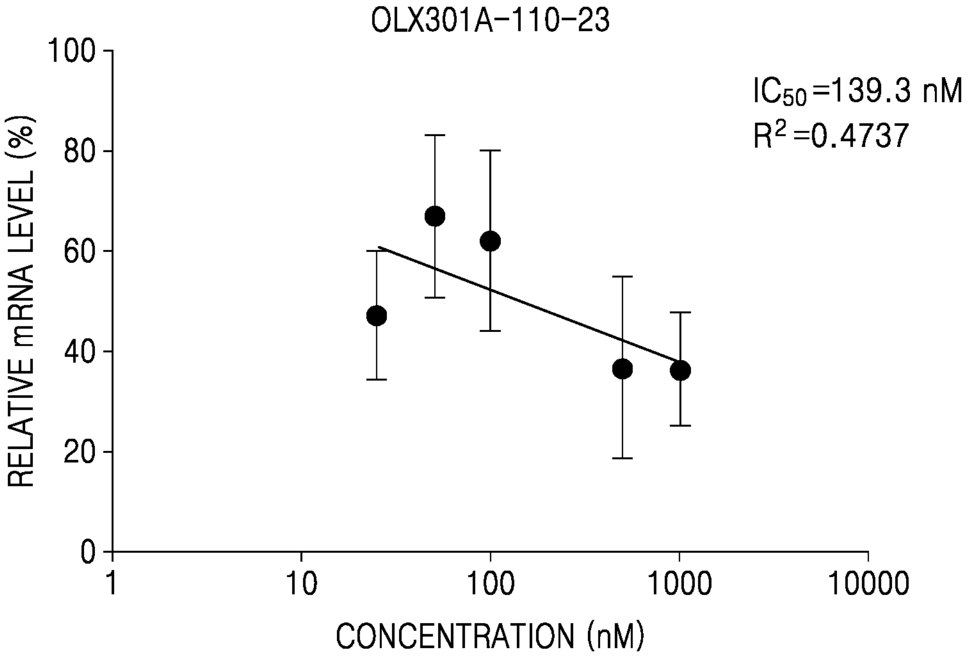

Y79 cells were treated with 25, 50, 100, 500, and 1000 nM of each siRNA and incubated (free uptake), and then expression levels of MyD88 mRNA were measured by real-time qPCR. Specifically, the Y79 cells were seeded on 24-well plates at a density of $6\times10^4$ cells/well. After 24 hours, 25, 50, 100, 500, and 1000 nM of siRNA was added thereto, and the cells were incubated under Opti-MEM media conditions, i.e., in an RPMI 1640 medium (10% FBS). After 24 hours, total RNA was extracted by using a Tri-RNA reagent (FAVORGEN), and cDNA was synthesized using a high-capacity cDNA reverse transcription kit (Applied Biosystems). Then, expression levels of MyD88 gene were identified by CFX Connect Real-Time PCR Detection System (BioRad) using TB Green Premix Ex Taq (Takara, RR420A) and primers shown in Table 6 (Refer to Table 7 and FIGS. 1A to 1C).

TABLE 6

| Name | | Sequence (5'→3') |
|---|---|---|
| Human | Forward | GCTCATCGAAAAGAGGTGCC (SEQ ID NO: 3) |
| MyD88 | Reverse | GGTTGGTGTAGTCGCAGACA (SEQ ID NO: 4) |

TABLE 7

| Concentration of | OLX301A-110-21 | | | | | OLX301A-110-22 | | | | |
|---|---|---|---|---|---|---|---|---|---|---|
| treated siRNA | 25 | 50 | 100 | 500 | 1000 | 25 | 50 | 100 | 500 | 1000 |
| Relative mRNA level(%) | 72 | 67.4 | 53.3 | 34.6 | 30.2 | 71.9 | 84.7 | 83.9 | 58.3 | 23.2 |

| Concentration of | OLX301A-110-23 | | | | |
|---|---|---|---|---|---|
| treated siRNA | 25 | 50 | 100 | 500 | 1000 |
| Relative mRNA level(%) | 47 | 66.6 | 61.9 | 36.6 | 36.2 |

Example 3. Evaluation of MyD88 Protein Level According to siRNA Treatment (1) Analysis According to Treatment with OLX301A-110-3, OLX301A-110-5, OLX301A-110-7, OLX301A-110-13, and OLX301A-110-14

In order to identify the effect of the siRNAs synthesized in Example 1 on inhibiting expression of MyD88 protein, ARPE-19 cells (ATCC) were transfected with 1 nM of each siRNA, and expression levels of MyD88 protein were measured by western blotting. Specifically, the ARPE-19 cells were seeded on 12-well plates at a density of $5\times10^4$ cells/well. After 24 hours, 2 μM of the siRNA was added thereto and the cells were incubated under Opti-MEM media conditions. After 24 hours, the medium was replaced with a Dulbecco's Modified Eagle's Medium/F-12 Nutrient Mixture Ham (DMEM/F-12) 1:1 Mixture (Gibco) supplemented with 10% fetal bovine serum (FBS, Gibco). After 48 hours, expression levels of the MyD88 protein were measured.

TABLE 8

| | Type of siRNA | | | | |
|---|---|---|---|---|---|
| | OLX301A-110-3 | OLX301A-110-5 | OLX301A-110-7 | OLX301A-110-13 | OLX301A-110-14 |
| MyD88 protein level (% of PBS) | 56.9 | 22.3 | 46.1 | 94.2 | 61.7 |

As a result, as shown in Table 8 above, the inhibitory effect of the siRNA treatment on expression of the MyD88 protein was confirmed. Particularly, relatively excellent MyD88 protein-inhibiting efficiencies were observed.

(2) Knockdown Analysis of MyD88 Protein In Vivo According to Treatment with OLX301A-110-21, OLX301A-110-22, and OLX301A-110-23

1) Effect on Inhibiting Expression of MyD88 Protein in Normal Mice

Figure 2A:
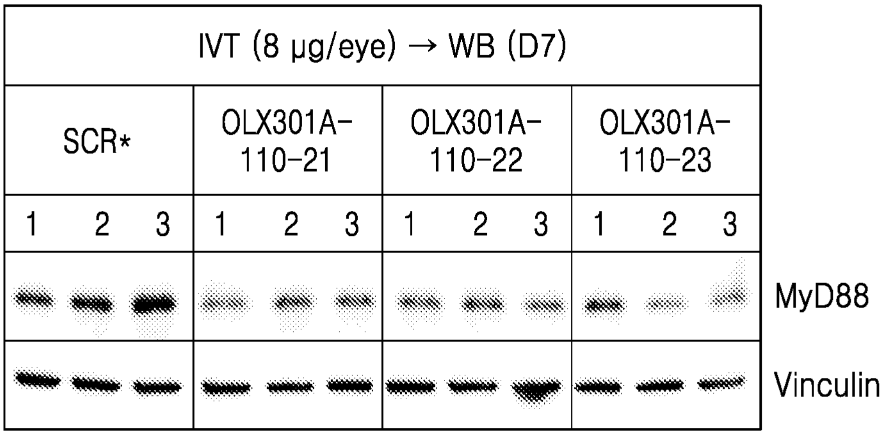
FIGS. 2A and 2B show changes in MyD88 protein levels of normal mouse models by treating with OLX301A-110-21, OLX301A-110-22, and OLX301A-110-23, which are siRNAs according to the present disclosure
Figure 2B:
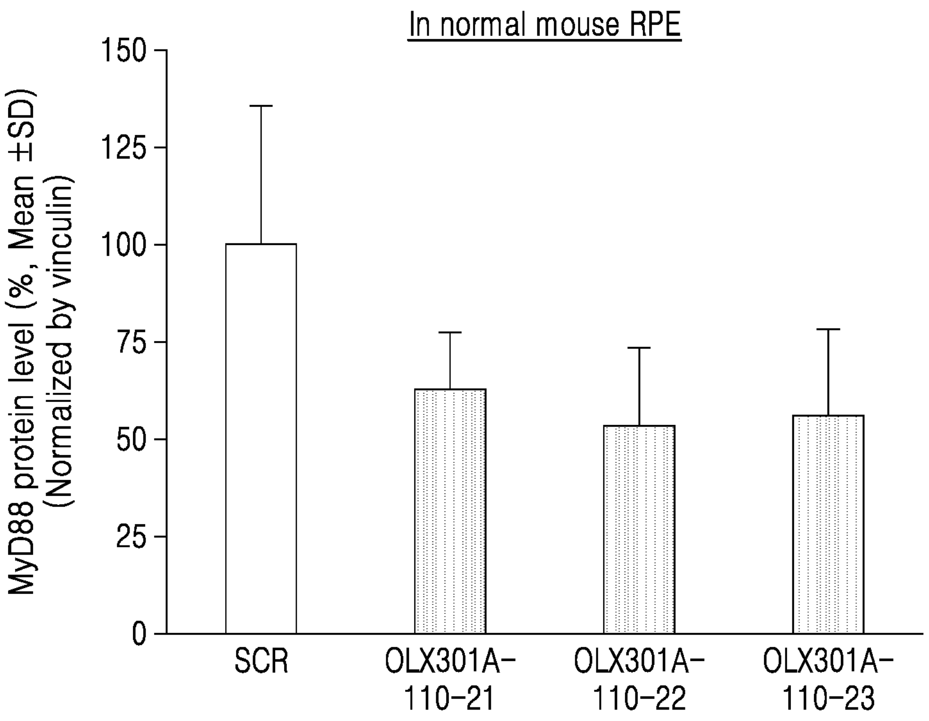

In the present example, experiments were performed as described below to identify whether the siRNAs synthesized in vivo in Example 1, OLX301A-110-21, OLX301A-110-22, and OLX301A-110-23, inhibit expression of MyD88 protein. In order to examine the effect on inhibiting expression of MyD88 protein in normal mice, 9-week-old male C57BL/6 mice (3 mice and 6 eyeballs per group) were administered with 0.8 μl of 10 mM PBS mixed solutions including 8 μg of OLX301A-110-21, OLX301A-110-22, and OLX301A-110-23, respectively via intravitreal injection (IVT) (Day 0). At 7th day after the administration, Retinal pigmented epithelium (RPE) was isolated from the mice, added to an RIPA buffer (SIGMA, R0278), and homogenized using a tissue grinder pestle (Scienceware, 199230001) and a sonicator (Sonics, VC505). Subsequently, protein included in a supernatant obtained by centrifugation was quantified using a BCA Protein Assay Kit (Thermo, 23225), 20 μg of the protein of each sample was electrophoresed using a 8% to16% Precast Gel (Bio-rad, 456-1106) and transferred to a PVDF membrane (Bio-rad, 1620177). The resultant was blocked with a SuperBlock™ (TBS) blocking buffer (Thermo, 37535) and reacted using MyD88 antibody (1:500; Cell signaling, 4283) and Vinculin antibody (1:2,000, Santa Cruz, sc-73614), and HRP-conjugated anti-rabbit and anti-mouse IgG (1:5,000; Santa Cruz, sc-2357 and Bethyl laboratories, A90-116P) according to protocols of respective manufacturers. Expression levels of MyD88 and Vinculin protein were identified via treatment with ECL (Thermo, 34580, or 34095) using ChemiDoc XRS+ (Bio-Rad, 1708265). Scrambled cp-asiRNA (SCR)-administered group was used as a negative control of the experiment. As a result, it was confirmed that the expression level of MyD88 protein decreased by about 35% to 45% (refer to Table 9 and FIGS. 2A and 2B)

TABLE 9

| | OLX301A-110-21 | OLX301A-110-22 | OLX301A-110-23 |
|---|---|---|---|
| MyD88 protein level (% of SCR) | 64.43 | 54.26 | 56.61 |
| SCR | sense strand (5'→3') ACACGCAGACUGUA*C*U*chol (SEQ ID NO: 17)<br>antisense strand (5'→3') AGUACAGUCUGCG*U*mG*mU*mU*mA*U (SEQ ID NO: 18) | | |

Figure 3A:
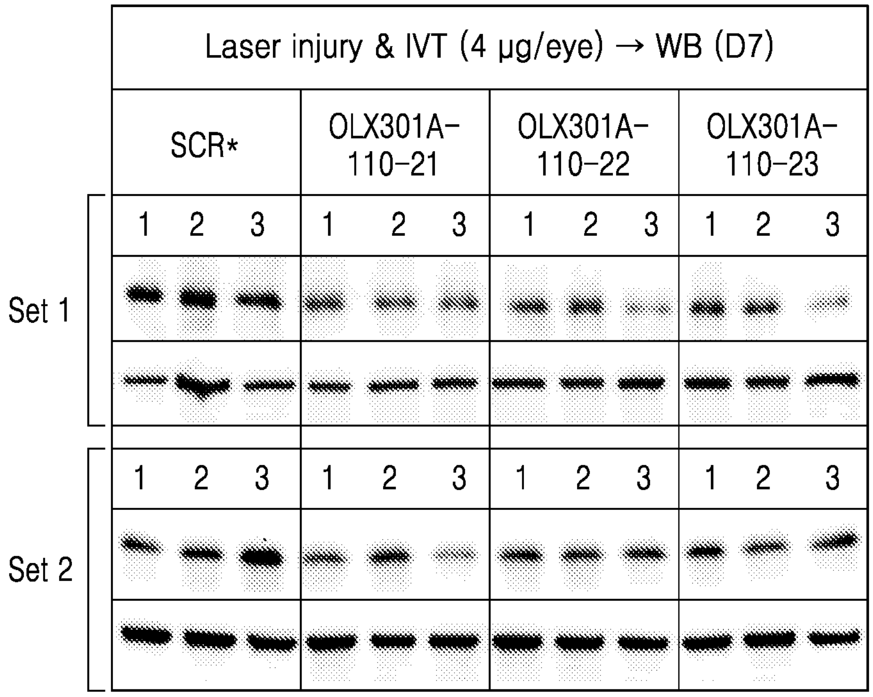
FIGS. 3A and 3B show changes MyD88 protein levels of laser-induced choroidal neovascularization (CNV) mouse models by treatment with OLX301A-110-21, OLX301A-110-22, and OLX301A-110-23 which are siRNAs according to the present disclosure.
Figure 3B:
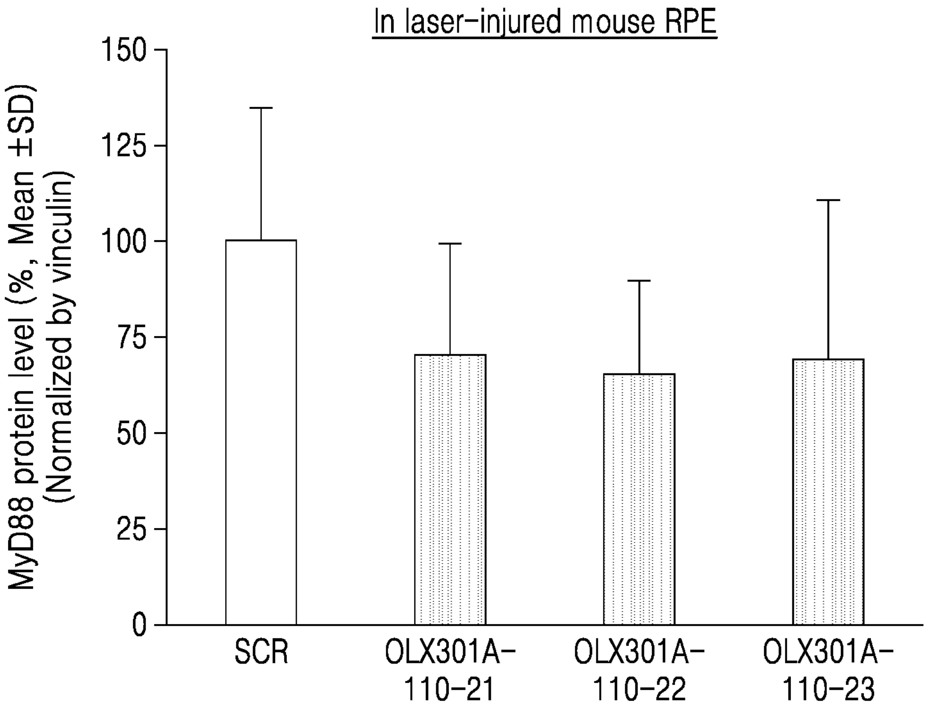

2) Effect on Inhibiting Expression of MyD88 Protein in Laser-Induced CNV Mouse Model In order to identify the effect of OLX301A-110-21, OLX301A-110-22, and OLX301A-110-23 on inhibiting expression of MyD88 protein in a Laser-induced CNV mouse model, immediately after causing a Laser injury (Power: 130 mW, Duration: 80 ms, Size: 75 μm, 6 lasers/eyeballs) in 9-week-old male C57BL/6 mice (6 mice and 12 eyeballs per group), the mice were administered with 0.8 μl of 10 mM PBS mixed solutions each including 4 μg of OLX301A-110-21, OLX301A-110-22, and OLX301A-110-23 by intravitreal injection (IVT) (Day 0). At 7th day after the administration, RPE was isolated from the mice in the same manner as described above and 20 μg of protein of each sample was subjected to Western blot analysis, thereby measuring expression levels of MyD88 protein. Scrambled cp-asiRNA (SCR)-administered group was used as a negative control of the experiment. As a result, it was confirmed that the expression level of MyD88 protein decreased by about 30% to 35% (Refer to Table 10 and FIGS. 3A and 3B).

TABLE 10

| | OLX301A-110-21 | OLX301A-110-22 | OLX301A-110-23 |
|---|---|---|---|
| MyD88 protein level (% of SCR) | 71.07 | 66.38 | 69.55 |

3) Confirmation of Decrease in CNV Volume in CNV Model

Figure 4:
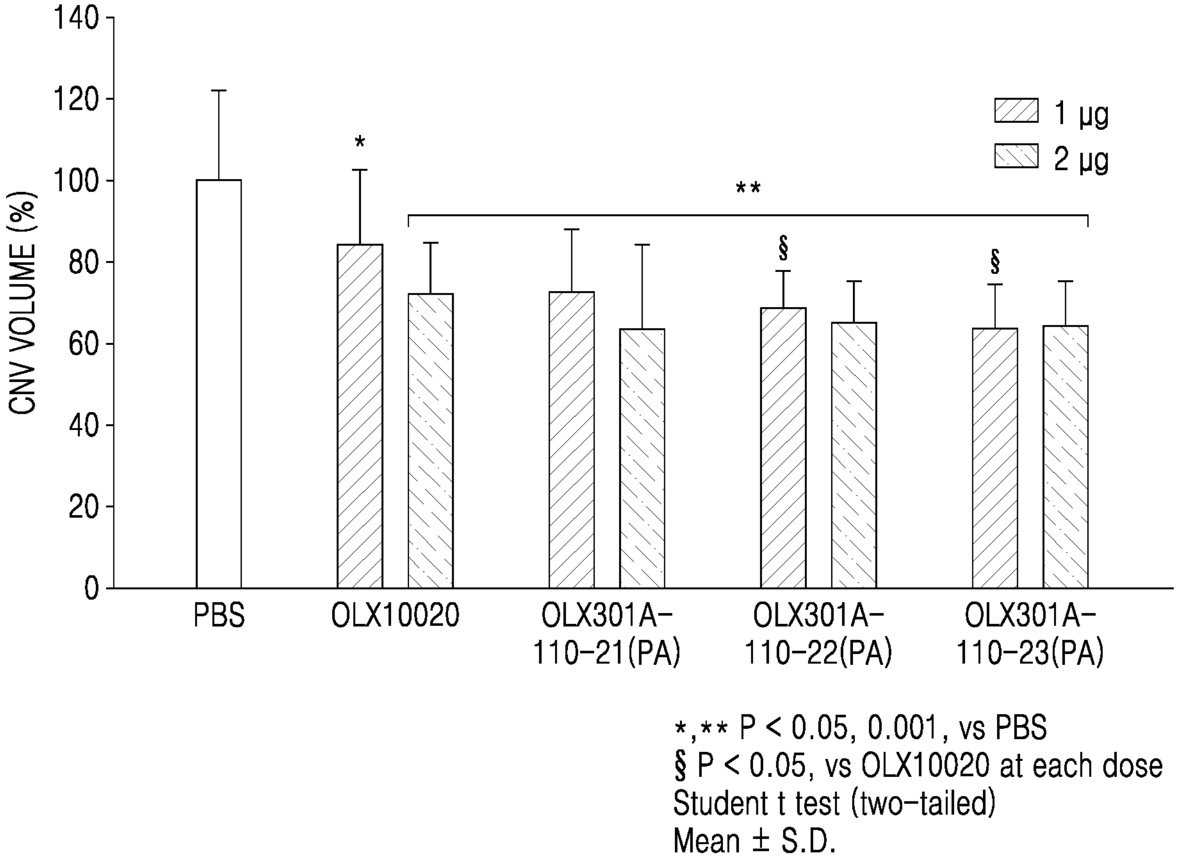
FIG. 4 shows volume changes of CNV by administration of OLX301A-110-21, OLX301A-110-22, and OLX301A-110-23, which are siRNAs according to the present disclosure, to a CNV mouse model.

In the present example, therapeutic effects of administration of OLX301A-110-21, OLX301A-110-22 and OLX301A-110-23 were evaluated in mice in which choroidal neovascularization (CNV) was induced by laser photocoagulation. Specifically, immediately inducing laser photocoagulation (Power: 130 mW, Duration: 80 ms, Size: 75 μm, 4 lasers/eyeball) in 9-week-old male C57BL/6 mice (8 mice and 8 eyeballs per group), 8 μg of 10 mM PBS mixed solutions including 1 μg and 2 μg of OLX301A-110-21, OLX301A-110-22, and OLX301A-110-23, respectively were prepared and administered thereto via intravitreal injection (IVT) (Day 0). At $6^{th}$ day therefrom, RPE flat isolated from the eyeballs of the mice was immunostained using a vascular endothelial cell-specific Isolectin B4 (Vector laboratories, FL-1201). Thereafter, the resultants were photographed from the beginning to the end of fluorescence using a confocal microscope (Leica, TCS SP8). The therapeutic effects were evaluated by measuring a volume of CNV by quantifying an area stained with IB4 from the obtained image using J software, and performing relative % comparison with a negative control. A 10 mM PBS-administered group was used as a negative control of the experiment, and groups administered with 1 μg and 2 μg of OLX10020 were used as positive controls. As a result, it was confirmed that the volume of CNV decreased by about 30% to 40% and better effect than the positive controls were confirmed (Refer to Table 11 and FIG. 4).

TABLE 11

| | OLX301A-110-21 | | OLX301A-110-22 | | OLX301A-110-23 | | Positive control | |
|---|---|---|---|---|---|---|---|---|
| Administered amount of cp-siRNA (μg) | 1 | 2 | 1 | 2 | 1 | 2 | 1 | 2 |
| CNV volum (% of 10 mM PBS) | 72.54 | 62.75 | 68.86 | 65.34 | 63.74 | 63.87 | 84.09 | 72.00 |
| Positive control OLX10020 | sense strand (5'→3') GUGACUUCCAGACC*A*A*chol (SEQ ID NO: 19) antisense strand (5'→3') UUGGUCUGGAAGU*C*mA*mC*mA*mU*U (SEQ ID NO: 20) | | | | | | | |

-

The above description of the present disclosure is provided for the purpose of illustration, and it would be understood by those skilled in the art that various changes and modifications may be made without changing technical conception and essential features of the present disclosure. Thus, it is clear that the above-described embodiments of the present disclosure are illustrative in all aspects and do not limit the present disclosure.

SEQUENCE LISTING

```
<160> NUMBER OF SEQ ID NOS: 20

<210> SEQ ID NO 1
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 1

uggucuggaa gucacauuc                                              19
```

-continued

<210> SEQ ID NO 2
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 2
ugugacuucc agacca 16

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 3
gctcatcgaa aagaggtgcc 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 4
ggttggtgta gtcgcagaca 20

<210> SEQ ID NO 5
<211> LENGTH: 19
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: The at least one chemical modification of SEQ ID NO: 5 are shown in Table 1 and Table 2 of the Specification.

<400> SEQUENCE: 5
uggucuggaa gucacauuc 19

<210> SEQ ID NO 6
<211> LENGTH: 19
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: The at least one chemical modification of SEQ ID NO: 6 are shown in Table 1 and Table 2 of the Specification.

<400> SEQUENCE: 6
uggucuggaa gucacauuc 19

<210> SEQ ID NO 7
<211> LENGTH: 19
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)

-continued

<223> OTHER INFORMATION: The at least one chemical modification of SEQ
      ID NO: 7 are shown in Table 1 and Table 2 of the Specification.

<400> SEQUENCE: 7
uggucuggaa gucacauuc 19

<210> SEQ ID NO 8
<211> LENGTH: 19
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: The at least one chemical modification of SEQ
      ID NO: 8 are shown in Table 1 and Table 2 of the Specification.

<400> SEQUENCE: 8
uggucuggaa gucacauuc 19

<210> SEQ ID NO 9
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ
      ID NO: 9 are, according to page 4 of the Specification, * is a
      phosphorothioate linkage, m is 2'-O-methyl, and Lp is a lipophilic
      moiety.

<400> SEQUENCE: 9
ugugacuucc agacca 16

<210> SEQ ID NO 10
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ
      ID NO: 10 are, according to page 4 of the Specification, * is a
      phosphorothioate linkage, m is 2'-O-methyl, and Lp is a lipophilic
      moiety.

<400> SEQUENCE: 10
ugugacuucc agacca 16

<210> SEQ ID NO 11
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ
      ID NO: 11 are shown in Table 1 and Table 2 of the Specification.

<400> SEQUENCE: 11
ugugacuucc agacca 16

-continued

<210> SEQ ID NO 12
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ ID NO: 12 are shown in Table 1 and Table 2 of the Specification.

<400> SEQUENCE: 12
ugugacuucc agacca 16

<210> SEQ ID NO 13
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ ID NO: 13 are shown in Table 1 and Table 2 of the Specification.

<400> SEQUENCE: 13
ugugacuucc agacca 16

<210> SEQ ID NO 14
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ ID NO: 14 are shown in Table 1 and Table 2 of the Specification.

<400> SEQUENCE: 14
ugugacuucc agacca 16

<210> SEQ ID NO 15
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ ID NO: 15 are shown in Table 1 and Table 2 of the Specification.

<400> SEQUENCE: 15
ugugacuucc agacca 16

<210> SEQ ID NO 16
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ ID NO: 16 are shown in Table 1 and Table 2 of the Specification.

<400> SEQUENCE: 16
ugugacuucc agacca 16

<210> SEQ ID NO 17
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ ID NO: 17 are, according to page 4 and page 10 of the Specification, * is a phosphorothioate linkage, and chol is 3'-cholesterol linkage.

<400> SEQUENCE: 17
acacgcagac uguacu 16

<210> SEQ ID NO 18
<211> LENGTH: 19
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)
<223> OTHER INFORMATION: The at least one chemical modification of SEQ ID NO: 18 are, according to page 4 and page 10 of the Specification, * is a phosphorothioate linkage, and chol is 3'-cholesterol linkage.

<400> SEQUENCE: 18
aguacagucu gcguguuau 19

<210> SEQ ID NO 19
<211> LENGTH: 16
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(16)
<223> OTHER INFORMATION: The at least one chemical modification of SEQ ID NO: 19 are, according to page 4 and page 10 of the Specification, * is a phosphorothioate linkage, and chol is 3'-cholesterol linkage.

<400> SEQUENCE: 19
gugacuucca gaccaa 16

<210> SEQ ID NO 20
<211> LENGTH: 19
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(19)

-continued

<223> OTHER INFORMATION: The at least one chemical modification of SEQ ID NO: 19 are, according to page 4 and page 10 of the Specification, * is a phosphorothioate linkage, and chol is 3'-cholesterol linkage.

<400> SEQUENCE: 20
uuggucugga agucacauu 19

The invention claimed is:

1. A double-stranded RNAi-inducing nucleic acid molecule comprising a sense strand and an antisense strand, wherein:

the sense strand is 15 to 17 nucleotides in length; at least 15 contiguous nucleotides of the sense strand are complementary to the antisense strand; the sense strand comprises at least one chemical modification; and the antisense strand comprises a sequence selected from the group consisting of (A) to (D) (5'->3'):

(A)
(SEQ ID NO: 5)
P-mUGGUCUGGAAGmUmCAmC*A*mU*mU*mC, (B)
(SEQ ID NO: 6)
P-mUfGmGfUmCfUmGfGmAfAmGfUmCfAmC*fA*mU*fU*mC, (C)
(SEQ ID NO: 7)
P-mUGmGUCUmGmGmAmAmGUCAC*mA*U*U*C,
and (D)
(SEQ ID NO: 8)
P-mUGGfUfCfUGGAAGfUfCAfC*A*fU*fU*fC, wherein * is a phosphorothioate linkage, m is 2'-O-methyl, f is 2'-fluoro, and P is a 5'-phosphate linkage.

2. A double-stranded RNAi-inducing nucleic acid molecule comprising a sense strand and an antisense strand, wherein:

the antisense strand is 19 to 21 nucleotides in length; at least 15 contiguous nucleotides of the antisense strand are complementary to the sense strand; the antisense strand comprises at least one chemical modification; and the sense strand comprises the sequence selected from the group consisting of (a) and (b) (5'->3'):

(a)
(SEQ ID NO: 15)
mUmGUGACUUCCAGAC*mC*mA*Lp,
and (b)
(SEQ ID NO: 10)
mUGmUGAmCmUmUmCmCAGAmC*mC*A*Lp, wherein * is a phosphorothioate linkage, m is 2'-O-methyl, and Lp is a lipophilic moiety.

3. The RNAi-inducing nucleic acid molecule of claim 1 or 2, wherein the RNAi-inducing nucleic acid molecule is siRNA.

4. The RNAi-inducing nucleic acid molecule of claim 1 or 2, wherein the chemical modification is selected from:

a modification of at least one nucleotide bond into a phosphorothioate bond;

a modification in which an —OH group at a 2' carbon position of a sugar structure in a nucleotide is substituted with —$OCH_3$ (methoxy); or an introduction of a lipophilic moiety at a 3'-end of the sense strand, the lipophilic moiety being selected from the group consisting of cholesterol, tocopherol, stearic acid, retinoic acid, docosahexaenoic acid (DHA), palmitic acid, linoleic acid, linolenic acid, and a long-chain fatty acid of at least 10 carbon atoms.

5. The RNAi-inducing nucleic acid molecule of claim 1 or 2, wherein the RNAi-inducing nucleic acid molecule has an asymmetric double strand structure, and a 5'-end of the antisense strand and a 3'-end of the sense strand form a blunt end.

6. The RNAi-inducing nucleic acid molecule of claim 1 or 2, wherein the RNAi-inducing nucleic acid molecule inhibits expression of myeloid differentiation primary response gene 88 (MyD88).

7. A pharmaceutical composition for treating age-related macular degeneration, comprising the RNAi-inducing nucleic acid molecule of claim 1 or 2 as an active ingredient.

8. A method of treating age-related macular degeneration in a patient, the method comprising administering the pharmaceutical composition of claim 7 by intravitreal administration to the eye of the subject.

* * * * *